United States Patent [19]

Blanchette et al.

[11] Patent Number: 5,055,159

[45] Date of Patent: Oct. 8, 1991

[54] BIOMECHANICAL PULPING WITH C. SUBVERMISPORA

[75] Inventors: Robert A. Blanchette, Shoreview, Minn.; Gary F. Leatham, Madison; Michael Attridge, McFarland; Masood Akhtar; Gary C. Myers, both of Madison, all of Wis.

[73] Assignee: Wisconsin Alumni Research Foundation, Madison, Wis.

[21] Appl. No.: 523,956

[22] Filed: May 16, 1990

[51] Int. Cl.$^5$ .................... D21C 3/00; D21C 3/20; C12R 1/645

[52] U.S. Cl. .................................. 162/72; 162/13; 435/278

[58] Field of Search .................... 162/72, 72 B, 13; 435/171, 277, 278, 911

[56] References Cited

U.S. PATENT DOCUMENTS 3,962,033 6/1976 Eriksson et al.
4,687,745 8/1987 Farrel .................................. 435/278

OTHER PUBLICATIONS

Akamatsu, I. et al., "Influence of White-Rot Fungi on Poplar Chips and Thermomechanical Pulping of Fungi--Treated Chips," *Journal of Japan Wood Research Society*, 30(8) pp. 697-702 (1984) and translation.

Ander, P. and K. E. Eriksson, "Mekanisk massa fran forrotad flisen inledande undersokning," *Svensk Papperstidning*, 18:641 (1975).

Blanchette, R. A., "Screening Wood Decayed by White-Rot Fungi for Preferential Lignin Degradation," *Applied & Environmental Microbiology*, 48(3):647-653 (1984).

Blanchette, R. A. and T. A. Burnes, "Selection of White-Rot Fungi for Biopulping," *Biomass*, 15:93-101 (1988).

Eriksson, K. E. et al., "A Scanning Electron Microscopy Study of the Growth and Attack on Wood by Three White-Rot Fungi and their Cellulase-Less Mutants," *Holzforschung*, 34:207-213 (1980).

Eriksson, K. E. and L. Vallander, "Properties of Pulps from Thermomechanical Pulping of Chips Pretreated with Fungi," *Svensk Papperstidning*, No. 6-1982 85 (1982) R33-R38.

Eriksson, K. E., "Swedish Developments in Biotechnology Related to the Pulp and Paper Industry," *Tappi*, pp. 46-55, Jul., 1985.

Kirk, T. K. and H-M Chang, "Potential Applications of Bioligninolytic Systems," *Enzyme Microb. Technol.*, 3:189-196 (1981).

Kirk, T. K. et al., "Biotechnicology: Applications and Implications for the Pulp and Paper Industry," *Tappi*, 66(5):45 (1983).

Leatham, G. F., "A Chemically Defined Medium for the Fruiting of *Lentinus edodes*,"*Mycologia*, 75(5):905-908 (1983).

Leatham, G. F. et al., "Energy Savings in Biomechanical Pulping," presented at Biotechnology in the Pulp and Paper Industry 4th International Conference, Raleigh, N.C., May 16-19, 1989.

Leatham et al., "Biomechanical Pulping of Aspen Chips: Paper Strength and Optical Properties Resulting from Different Fungal Treatments," preprint, Nov., 1988.

(List continued on next page.)

Primary Examiner—Karen M. Hastings
Attorney, Agent, or Firm—Quarles & Brady

[57] ABSTRACT

A method of using biological processes as a pretreatment step in combined biological and mechanical paper pulping process is described. The process uses a species of fungus, Ceriporiopsis subvermispora, which has not previously been used for this purpose. It has been found that even with a non-optimized system, and with the stationary holding of the wood chips during fungal incubation, that significant savings in energy usage in the pulping process can be achieved compared to conventional mechanical pulping while simultaneously achieving increased strength characteristics in the paper.

31 Claims, 1 Drawing Sheet

OTHER PUBLICATIONS

Myers et al., "Fungal Pretreatment of Aspen Chips Improves Strength of Refiner Mechanical Pulp," *Tappi*, pp. 105–108, May, 1988.

Nakasone, K.K., "Cultural Studies on *Poria cinerascens, P rivulosa*, and P. subvermispora," *Mycotaxon*, 13:105–111 (1981).

Otjen, L. et al., "Assessment of 30 White-Rot Basidiomycetes for Selective Lignin Degradation", *Holzforschung*, 41:343–349 (1987).

Otjen, L. and R. A. Blanchette, "Selective Delignification of Aspen Wood Blocks in Vitro by Three White-Rot Basidiomycetes," *Applied and Environmental Microbiology*, 50(3):568–572 (1985).

Sachs, I. B. et al., Biomechanical Pulping of Aspen Chips by Phanerochaete Chrysosporium; Fungal Growth Pattern and Effects on Wood Cell Walls, *J. Soc. of Wood Sci. and Tech.*, 21(4):331 (1989).

Samuelsson, L. et al., "Influence of Fungal Treatment of the Strength Versus Energy Relationship in Mechanical Pulping," *Svensk Papperstidning*, 83:221–225 (1980).

BIOMECHANICAL PULPING WITH C. SUBVERMISPORA

FIELD OF THE INVENTION

The present invention relates to the general field of paper manufacture and relates, in particular, to the use of biological agents in conjunction with mechanical processes to produce paper pulp from wood.

BACKGROUND OF THE INVENTION

In the manufacture of paper from wood, the wood is first reduced to an intermediate stage in which the wood fibers are separated from their natural environment and transformed into a viscous liquid suspension known as a pulp. There are several classes of techniques which are known, and in general commercial use, for the production of pulp from various types of wood. The simpliest in concept of these techniques is the so-called refiner mechanical pulping (RMP) method, in which the input wood is simply ground or abraded in water through a mechanical milling operation until the fibers are of a defined desired state of freeness from each other. Other pulping methodologies include thermo-mechanical pulping (TMP), chemical treatment with thermo-mechanical pulping (CTMP), chemi-mechanical pulping (CMP) and the so-called kraft or sulfate process for pulping wood. In all of these processes for creating pulps from wood, the concept is to separate the wood fibers to a desired level of freeness from the complex matrix in which they are embedded in the native wood.

Of the constituents of wood as it exists in its native state, the cellulose polymers are the predominate molecule which is desired for retention in the pulp for paper production. The second most abundant polymer to cellulose in the native wood, which is the least desirable component in the pulp, is known as lignin. Lignin is a complex macromolecule of aromatic units with several different types of interunit linkages. In the native wood, lignin physically protects the cellulose polysaccharides in complexes known as lignocellulosics, and those lignocellulosics must be disrupted for there to be marked enzyme accessibility to the polysaccharides, or to separate lignin from the matrix of the wood fibers.

It has been suggested that biological systems can be utilized to assist in the pulping of wood. A desirable biological system would be one which is intended to liberate cellulose fibers from the lignin matrix by taking advantage of the natural abilities of a biological organism. Research in this area has focused on a type of fungi referred to as white-rot wood decay fungi. These fungi are referred to as white-rot, since the characteristic appearance of wood infected by these fungi is a pale color, which color is the result of the depletion of lignin in the wood, the lignin having been degraded or modified by the fungi. Since the fungi appear to preferentially degrade or modify lignin, they make a logical choice for fungi to be utilized in biological treatments to pulp wood, referred to as biopulping.

Several reports have been made of attempts to create biopulping systems using white-rot fungi on a variety of wood fibers. Previous research has concentrated on a single, or relatively few, species of fungi. The most commonly utilized fungi in such prior systems is the white-rot fungi *Phanerochaete chrysosporium*, also referred to as *Sporotrichum pulverulentum*. Other fungi which have been previously used in such procedures include fungi of the genera *Polyporus* and *Phlebia*. The prior art is generally cognizant of the fact that attempts have been made to use biological organisms, such as white-rot fungi, as part of a process of treating wood, in combination with a step of either mechanical or thermal mechanical pulping of cellulose fiber.

An example of a teaching of a method of producing cellulose pulp is shown in U.S. Pat. No. 3,962,033 directed to the biopulping of cellulose utilizing white-rot fungi. The fungi utilized included both of naturally occurring wild-type strain cultures and also mutant strains produced which were intended to be cellulase-less, so as to reduce the amount of cellulose degraded by the organisms. Various types of wood were degraded with the fungi, and then were used as input materials for a thermo-chemical or mechanical pulping procedure. This patent disclosure discusses various techniques for making a cellulose pulp by depleting lignin while reducing the cellulose-decomposing action of the enzymes produced by these organisms in order to preserve the cellulose yield. Groups working with the inventors of said patent also had several other publications regarding use of such fungi for biomechanical pulping, e.g. Anders and Erikkson, *Svensk Papperstidning*, 18:641-2 (1975), Erikkson and Vallander, *Svensk Papperstidning*, 6:85:33-38 (1982). Unfortunately, the process never gained commercial acceptance, and has not been widely utilized. One of the difficulties is that most of the prior techniques for utilizing biological techniques for the pulping of paper have resulted in paper which has had only marginal strength increase or is weaker than papers made by more conventional processes.

In fact, while a certain amount is known about the interaction of lignin and cellulose in wood fibers, because of the extreme complexity of the relationships, and the variation in the enzymes produced by varieties of the white-rot fungi, it is not readily possible to predict from the action of a given fungi on wood whether or not the paper made from wood partially digested with such fungi will have desirable qualities or not. The selection of white-rot fungi for biopulping applications on the basis of selective lignin degradation may seem a rational one, but it has proven to be a poor predictor of the quality of the resultant paper. The exact relationship between the degradation of lignin, and the resulting desirable qualities of paper produced at the end of the pulping process, are not at all clear. Accordingly, given present standards of technology and the present understanding of the complex interaction of lignin and cellulose, it is only possible to determine empirically the quality of paper produced through a given biological pulping process and the amount of any energy savings achieved through such a process.

SUMMARY OF THE INVENTION

The present invention is summarized in that a method for the biomechanical pulping of paper involves the partial degradation of wood with a culture of the fungus *Ceriporiopsis subvermispora* followed by mechanical pulping of the treated wood.

It has been found that through the biological degradation of the wood chips using *Ceriporiopsis subvermispora* followed by mechanical pulping of the treated wood chips that a dramatic decrease in the energy required for mechanical pulping is achieved while at the same time giving rise to paper which has enhanced, rather than decreased, strength characteristics.

It is thus an advantage of the process described in accordance with the present invention that a procedure for the biomechanical pulping of wood chips is described which utilizes less energy than prior art techniques and which results in paper having more desirable strength characteristics.

It is further an object of the present invention in that it utilizes a natural biological organism to degrade the wood thus reducing the likelihood of unwanted artificial environmental contaminants produced by degradation of lignin and its byproducts.

It is a further advantage of the present invention in that it has been found that the biological processing of the wood chips in accordance with the present invention can be done in a static fermentation procedure without the need for an exotic or moving fermenting chamber thereby allowing the process to be used more practically on a large scale.

Other objects, advantages, and features of the present invention will become apparent from the following specification when taken in conjunction with the accompanying drawings.

DESCRIPTION OF THE INVENTION

The present invention is directed toward the biological pretreatment of wood chips for pulp making for paper manufacture. It has been particularly found here that through the use of a particular species of fungus, and the maintenance of relatively forgiving conditions during the treatment of wood chips by said fungus, it is possible to utilize a biological treatment or pretreatment as a part of a pulping process on Southern Yellow Pine, a tree resource of high commercial importance in the United States. It has further been found that the process results in a paper which has a strength which is increased over paper made by purely mechanical pulping but which, at the same time, results in a dramatic savings in the energy expended during the mechanical pulping process. In other words, the process not only results in energy saving, it also results in a stronger product.

The present process makes use of a saprophitic fungi of the white-rot class of wood decay fungus. The particular species of fungus which is found useful within the present invention is *Ceriporiopsis subvermispora*. The particular strain of *C. subvermispora* utilized in the examples below, FP-90031 was obtained from the Center for Forest Mycology Research (CFMR) from the United States Department of Agriculture Forest Products Laboratory in Madison, Wis. The original depositor of this strain with the CFMR reported that the culture was isolated from an oak log in Prince Georges County, Md. This fungus was selected from the CFMR selection through a process of both selection and screening. It was desired that a fungus be selected for a biological pulping operation which would propagate relatively rapidly through wood chips in culture. The need for rapidity was due to the fact that the length of the dwell time of the wood chips in a bioreactor would add to the capital costs of an overall biopulping process. Therefore, fungi which could proliferate through a given volume of wood chips in the shortest period of time possible would be desired. In addition, it was also desired that the fungus be considered to be a relatively selective lignin degrader, but not a significant degrader of cellulose. It was theorized that such a lignin degrader would preferentially modify or remove lignin from the wood and leave the cellulose, the cellulose being the more desired component for paper fiber.

However, empirical screening results revealed that neither speed of propagation through wood, nor the preference for lignin degration over cellulose degradation, alone, were sufficient factors to be able to predict the efficacy of a fungi in a biopulping process. Fungi which proved to be fast in the propagation through wood chips occasionally resulted in paper of inferior quality or strength or gave little energy savings in the overall process. Some of the fungi which preferentially degraded lignin over cellulose proved to be very slow growing, and thus ineffective for use in a biopulping process.

It was found that the particular fungi described herein, *Ceriporiopsis subvermispora*, was particularly well suited for biopulping applications. It is a preferential lignin degrader. If a culture of *C. subvermispora* is grown on a wood chip, the wood chip will suffer significant loss of lignin with a relatively low loss of total weight from the chip. *C. subvermispora* is also a reasonably fast grower, although not among the fastest growing of the strains subjected to this screening technique.

*C. subvermispora*, also previously known as *Poria subvermispora*, is a white-rot saprophytic fungi widely distributed throughout the continental United States. It is associated with a white rot of both conifers and hardwoods and has been isolated several times from wood chip piles in Washington and Oregon. It is related to, but is distinct from, *Phlebia* species. It has not previously been known to have industrial value. Some of Nakasone, *Mycotaxon*, 15:105–111 (1981).

The screening utilized herein was based on an intelligent selection of fungi having a reasonable likelihood of being applicable to biopulping, plus an empirical testing of the eligible fungi to determine those strains which were most advantageous for the procedure. Accordingly, an extensive investigation was conducted, principally through the records of the Center for Forest Mycology Research of the Forest Products Laboratory in Madison, Wis., to identify previously isolated fungi which appeared to have potentially desirable characteristics for biopulping applications. Approximately 50 or 60 strains of such fungi were identified. Those strains were then screened through a testing procedure desired to determine which of those strains were preferential lignin degraders and to rank the strains relative to each other regarding the speed of degradation achieved by the particular strain. The testing was conducted on wood blocks of both Pine and Aspen. After the treatment of the wood blocks with the test fungi, the blocks were analyzed both for remaining lignin content and for overall weight. In addition, loss of other important sugars was measured as an indication of loss of cellulose component.

From the screening procedure on the wood blocks, a relatively small number of fungi were selected for the actual use in a test biopulping process. Those fungi were used to actually inoculate wood chips in culture, and were permitted to ferment throughout the wood chips. After a suitable fermentation period, the wood chips were mechanically pulped to a series of desired steps of freeness. The energy utilized in each of the mechanical pulping procedures was carefully monitored. As batches of pulps reached a desired level of standard freeness, paper was made from the pulps using standard handsheet making techniques. The paper resulting from such a process could be subjected to standard tests for tear and burst strength. Those results could then be compared to the energy values required for achieving the desired freeness in various batches of treated material which had been pretreated with the different wood rot fungi. Through such a procedure it was determined that a fungus of a particular species not only resulted in paper which had significantly increased strength as measured by standard techniques, but also had required significantly less input energy during the mechanical pulping procedure to achieve the same desired levels of freeness. That fungus was *Ceriporiopsis subvermispora*.

It is now appropriate to describe the general perimeters of biopulping process performed in accordance with the protocol of the present invention. The process begins, of course, with wood chips. While the process of the present invention, and in particular the utilization of the particular fungal species disclosed herein, is intended and particularly adapted for the biopulping of U.S. Southern Pine species, it has also been found that the fungus has utility for hardwood species, such as Aspen, in addition. A preferred species for use in the biopulping process of the present invention is Loblolly Pine, *Pinus taeda*. The pine is prepared in chips through a conventional technology to a chip size of anywhere between ⅛ and ¾ of an inch, but most preferably in the range of approximately ¼ inch. Chip sterilization prior to the fungal inoculation process may or may not be required. If required, chip sterilization can be achieved by heat pasteurization or chemical or steam autoclaving. Since conditions of high humidity during the fermentation process will be desired, a relatively high moisture content in the chips prior to fermentation is most desirable. Therefore it is desired that the chip moisture content prior to inoculation be at the fiber saturation point or greater. A preferred moisture content would be approximately 65% of the total wood, based on the oven dry weight of the chips. This measurement indicates that of the total weight of the moist wood, approximately 65% of that weight is moisture.

It is possible that nutrient amendments to the chips may be desirable to achieve the greatest efficiency in the fungal penetration of the wood chips. If such amendments are utilized, the amendment should have a relatively low component of nitrogen source, between 0% and 2% nitrogen on the basis of the dry chip weight. The preferred nitrogen content for such a chip amendment is 0.0035% plus or minus two fold. A carbon source may also be used in the chip amendment of significantly greater content, between 0% and 5% on the basis of dried chip weight, with a preferred range of approximately 2-4% of the chip amendment. Minerals or vitamins important to the nutrient needs of the fungal culture may also be supplied in ranges of less than 0.02% each of the chip amendment.

Separately from the chips, a seed inoculum must be maintained of the culture to be utilized during the biopulping process. The preferred culture here would be that of fungal species *Ceriporiopsis subvermispora*, with the preferred strain identified to date being strain FP-90031 from the Center for Forest Mycology Research of the Forest Products Laboratory. Strains of *Ceriporiopsis subvermispora* can be maintained on conventional fungal culture techniques, most conveniently potato dextrose agar (PDA) slants. Stock slants may routinely be prepared from an original culture for routine use and may be refrigerated until used.

To inoculate significant volumes of wood chips, a starter inoculum must be prepared. The starter inoculum is simply a smaller volume of chips carrying the fungal mycelium propagated therethrough so that it may be conveniently mixed into a larger volume of chips for the inoculation of the larger quantity of wood chips to be subjected to the process. In the laboratory-scale procedures described below, a plate culture was created using wood chips which were inoculated from the stock culture on a PDA slant. The plate cultures were created with wood chips, and a chemically defined medium A seed inoculum container has soaked wood chips added to it, and has been inoculated with a sector cut from the PDA culture of the fermenting microorganism. The chips are mixed and the seed inoculum container is incubated for a time period. The time period for seed culture incubation may be between 2 weeks and 4 weeks. In the seed inoculum culture, a relatively high moisture content in the wood, at least 60% is maintained to ensure better colonization of the chips with the fungal mycelia.

The actual inoculation of the chips for fungal degradation may then proceed. The wood chips for procedure are placed in the fermentation reactor. The reactor may be any of a number of styles of bioreactors capable of containing solid media fermentation cultures. Though it has been found that rotating drum bioreactors host the fermentation reaction to a sufficient degree, it has also been advantageously found that stationary or static reactors work sufficiently well within the present invention to be preferred. It is merely required that the stationary or solid phase reactor have sufficient aeration so as to ensure adequate oxygen flow to the fungus and significant removal of carbon dioxide therefrom. In fact, it is an advantage of the process described herein that a stationary, and even rudimentary, reactor will suffice. Since what is required is simply aeration, humidity, and temperature control, it is envisioned that simple pits or piles of chips on the ground may be utilized if aeration is provided, as by inserted tubing, and humidity is maintained, either by containment or by moisture application.

The inoculation of the starter inoculant culture is made to the wood chips to be treated. The amount of inoculum starter culture added to the chips can vary between 1% and 25%, on a dry weight basis, of the total volume of the chips. It is preferred that generally on the order of 2-10% of the volume of chips to be treated should be the volume of starter inoculation culture added to the chips to be degraded. The starter inoculum culture chips and the chips to be treated should be thoroughly mixed and placed into the bioreactor for degradation.

The chips so inoculated will then be fermented during a time period in which the fungal mycelia will penetrate throughout the wood chips and culture. The temperature range most desired depends on the fungal strains. It has been found that a bioreactor kept in the range of 27° C. plus or minus two degrees with a moisture content in the wood of 65% plus or minus 5% achieves a degree of mycelia penetration of the wood chips that results in significant and useful degradation of the chips for paper pulping purposes. Continually during the incubation period the wood chips are preferably aerated with moisture saturated air such that the wood maintains the constant moisture content of 65%. It is most desired if the pH of the chip incubation culture is specifically monitored so that it is ensured that the pH stays within the broad range of between 3.0 and 6.0. Thus it is not required that pH be specifically controlled, but only monitored on occasion so that it remains within the physiological limits necessary for the growth of the fungal culture.

The time period of fungal incubation with the wood chips will vary depending on the economics of the installation. To some degree, the length of the fungal incubation will have an effect on the amount of energy saved during the subsequent mechanical refining process. In usual terms, up to certain limits, the longer the period of dwell in the incubation reactor, the less energy required for the mechanical pulping of the wood thereafter. It has been found that an incubation period of four weeks results in significant modification of the wood chips and useful energy savings in the subsequent mechanical refining steps. It is also believed that incubation periods of as short as two weeks may be useful in providing significant energy savings in a commercial scale biopulping process. What is required to benefit from this process is only that a significant portion of the lignin in the wood is removed or modified such that the treated wood chips when pulped yield an acceptable level of energy savings compared to untreated chips. Obviously with a longer incubation period, capital costs can be higher, so although energy costs will be lower with longer incubation, economic factors may determine the length of incubation for a particular implementation.

After the incubation of the fungi in the wood chips, the wood chips are then subjected to a more conventional refining process to make wood pulp of the desired level of freeness. In its simplest form, a mechanical refining process is utilized. Dilution water is added to the chips and the chips are run through a mechanical refiner through a number of passes. The number of passes of the chips/pulp mixture will depend upon the freeness desired for the particular paper application to be made. The chip/pulp mixture is fed through the refiner until the desired level of freeness is achieved. Thus freeness may be periodically monitored to determine the progress of the pulps toward the freeness level which is desired for the paper. Between passes the wood pulp may be dewatered as necessary. It has been found that Loblolly Pine which has been incubated for a time period of four weeks with the fungal culture described above requires between ten and fifteen passes to obtain the value of 100 ml Canadian standard freeness in a single disk mechanical refiner with an initial setting of 18 mils.

The overall energy efficiency of the process can be compared to a straight mechanical process by pulping in the same apparatus either untreated chips or treated chips while at the same time monitoring the energy consumption of the refining mill itself. It will be found that the treated chips require significantly less energy input through the refiner to achieve the same level of freeness in the resulting pulps.

The biomechanical pulps made through this procedure may then be made into paper using standard paper making techniques. It has been found that the standard techniques as described by the Technical Association of the Paper and Pulp Industry (TAPPI) which are known to work with mechanically refined pulps work equally well with the biomechanically refined pulps of the type created by the process described herein. Accordingly, the paper may be made in conventional methodologies. The paper from the biomechanically created pulp can be compared in quality, strength and texture to that created through simple mechanical pulping and it will be found that the biomechanically created pulp has significantly increased strength properties. Thus it is apparent that the process of the present invention does not sacrifice the quality or strength of the paper in order to achieve the highly desirable energy savings, but in fact results in a unique combination of both significant reduction in energy utilization in the process, and an increase in the strength properties of the resulting paper.

The details of the process of the present invention will become more apparent from the following example which describes the laboratory scale utilization of the present process and the results achieved thereby. While it is understood that the scale-up from a laboratory scale to a plant scale process of the pulping operation described below may involve some alteration of the perimeters or details of the process steps described herein. It is to be understood that the example described below, while it demonstrates the efficacy and practicability of the process of the present invention has not been optimized for a commercial scale. Nevertheless, the experimental evidence presented makes it clear that the procedure is efficacious and efficient and enables the creation of commercial scale procedures for implementing the general process described herein.

EXAMPLES

Screening of Fungi

A search was conducted through the fungal cultures on deposit with the Center for Forest Mycology Research, USDA Forest Products Laboratory. The records on available cultures were initially screened for fungal species which were known to be relatively selective for lignin degradation relative to cellulose degradation and which were relatively fast growing species. The screening also emphasized fungal species which were hosted well on pine species.

The initial screening was performed by culturing samples of the fungi on wood blocks. Initial investigations were conducted with birch and pine (*Pinus strobus* L) blocks. Wood blocks (1.6×1.6×0.7 cm) were cut from freshly harvested bolts, dried for 72 hours at 60° C. and weighed. The blocks were then placed in 30 ml glass bottles containing 10 ml vermiculite to which 5 ml of distilled water was added. The bottles were capped and autoclaved, then inoculated with a mat of mycelium of various fungal species. The blocks were incubated in the dark at 27° C. for 12 weeks at 90% humidity. After incubation, sample blocks were stained with phloroglucinol-HCl to detect lignin. The mycelium was removed from the remaining blocks and the blocks were reweighed. Lignin and sugar analysis were performed. These procedures and the results were reported in Otjen et al., *Holzforshung*, 41:6:343–349 (1987).

The results of this initial screening indicated that the percentage of wood degradation and the ratio of lignin to cellulose degradation varied a great deal from fungi to fungi. Most prior art attempts at biopulping had focussed on the fungi *Phanerochaete chrysosporium*, or one or more species of *Phlebia*. The results reported by Otjen et al., *supra*, suggested that while *P. chrysosporium* was particularly suitable for Aspen degradation, other fungi seemed better adapted for pine. The results of this screening for *Ceriporiopsis subvermispora* was that it was low to intermediate in total weight loss of wood but relatively high in the ratio of lignin to cellulose degraded.

Further screening was conducted among the most promising fungi in loblolly pine (*Pinus taeda* L.). Again wood blocks (1.6×1.6×0.7 cm) were dried for 72 hours at 60° C. and weighed. The blocks were moistened with distilled water and placed in 30 ml glass bottles (height 5.0 cm, diameter 3.5 cm) containing 10 cc vermiculite. Five ml of distilled water was added to each bottle. The bottles were autoclaved and cooled. The wood blocks were then inoculated with fungal mycelium from culture vials. The fungal inocula were grown in culture vials containing 6 ml malt yeast broth (15 g Difco malt extract, 2 g Difco yeast extract, 1000 ml distilled water). The inoculant mycelium was lifted from the vial, without broth, and placed on the wood block. There were ten blocks for each treatment, and ten uninoculated blocks for controls. The bottles were loosely capped and incubated in the dark at 27° C. and 90 relative humidity for 12 weeks. After incubation, the blocks were dried to determine the percentage of dry weight loss, and lignin and sugar analysis was conducted by the methods of Effland, *TAPPI*, 60:143-144 (1977) and Petterson et al., *J. Chromatogr. Sci.*, 22:478-484 (1985).

The results are presented in the following Table 1.

TABLE 1

Fungal Degradation of Loblolly Pine

| Species | Weight Loss (%) | Lignin Loss (%) | Glucose Loss (%) | Xylose Loss (%) | Mannose Loss (%) |
|---|---|---|---|---|---|
| *Ceriporiopsis subvermispora* | 23 | 38 | 14 | 30 | 17 |
| *Hyphodontia setulosa* | 13 | 25 | 6 | 15 | 18 |
| *Mycoacia fusco*-atra | 21 | 30 | 17 | 25 | 18 |
| *Phlebia brevispora* | 21 | 40 | 10 | 29 | 21 |
| *Dichomitus squalens* | 30 | 39 | 18 | 39 | 18 |
| *Ganoderma* sp. | 14 | 20 | 14 | 21 | 8 |
| *Phanerochaete chrysosporium* | 11 | 17 | 15 | 29 | 3 |
| *Phellinus pini* | 14 | 30 | 9 | 33 | 12 |
| *Phlebia tremellosa* | 17 | 36 | 13 | 29 | 10.1 |
| *Trametes versicolor* | 20 | 27 | 21 | 27 | 9 |

These results suggested that several of the fungal species offered potential for a biomechanical pulping process. Several of the species seemed to grow at significant rates and preferentially degrade lignin. The quality of the species as agents for biomechanical pulping could only be determined by making paper from pulps made using wood chips degraded by the fungi. After that procedure, as described below, was performed, the fungal species *Ceriporiopsis subvermispora* was found to have enabled a result dramatically better both in energy savings and paper strength compared to other fungal agents. Based on that conclusion, a testing of available strains of *C. subvermispora* was conducted to compare if other strains of the same species to the one used in the above experiment, strain Fp-90031. For this test, the wood blocks were prepared, inoculated, incubated and tested just as was done in the test with the various fungal species described above. The results of this test, using nine different strains of fungi of the species, is summarized in the following Table 2.

TABLE 2

*Ceriporiopsis subvermispora* Strains Degrading Loblolly Pine

| Strain | Weight Loss (%) | Lignin Loss (%) | Glucose Loss (%) | Xylose Loss (%) | Mannose Loss (%) |
|---|---|---|---|---|---|
| ME-485 | 22.8 | 31.0 | 20.3 | 0 | 24.2 |
| L-14807 | 22.5 | 37.0 | 14.7 | 33.2 | 29.9 |
| L-15225 | 23.7 | 38.2 | 12.4 | 27.2 | 28.1 |
| Fp-104027 | 28.3 | 40.6 | 18.8 | 33.8 | 26.9 |
| L-3292 | 29.0 | 42.2 | 22.4 | 31.1 | 26.2 |
| Fp-105752 | 19.6 | 33.9 | 7.1 | 27.0 | 10.1 |
| Lz-3 | 21.3 | 31.8 | 14.0 | 31.0 | 20.3 |
| L-6133 | 30.1 | 34.1 | 26.2 | 34.0 | 18.9 |
| Fp-90031 | 22.7 | 38.2 | 14.1 | 30.0 | 15.9 |

While, as noted above, evidence of the degrading effects of fungi on wood blocks are not determinative of the quality of paper produced from wood degraded by the fungi, these results suggest that the various *Ceriporiopsis subvermispora* strains have approximately similar effects on wood and therefore also suggest that similar advantages in the biopulping of paper are achievable as with the originally tested strain Fp-90031.

Other testing with the same methodology was conducted with a variety of strains of both *Phelbia tremellosa* and *Phanerochaete chrysosporium* on wood chip of Loblolly pine. For the *P. tremellosa* strains, the weight loss in the wood chips varied between 14 and 19% while the rate of lignin loss was between 19 and 30%. For the *P. chrysosporium* strains, weight loss varied between 1 and 21.8% and lignin loss varied between 11.0 and 22.9%. These results confirm the suggestion that all identified *C. subvermispora* strains are more efficient wood treating agents in pine than even the best *Phlebia* or *Phanerochaete* strains, suggesting again that the strains of *C. subvermispora* are likely to generally be superior agents for biopulping of pines compared to other prior fungi suggested for this application.

Inoculation and Incubation of Wood Chips

The wood chips used were from Southern Yellow Pine, or Loblolly pine, logs harvested from Bienville National Forest in Mississippi. The logs were debarked and chipped to about ¼ inch (6 mm) in size. The wood chips were bagged in plastic bags and frozen until use to prevent growth of contaminating fungi.

A culture of *Ceriporiopsis subvermispora*, strain Fp-90031, was maintained in serial culture on potato dextrose agar (PDA) slants. Stock slants were routinely prepared from the Center for Mycology Research collection culture. Working cultures were prepared from the stock culture for routine use. The slants were routinely refrigerated at 4° C. until used.

To begin an inoculum preparation, PDA plate cultures were inoculated from the working stock culture. The plate cultures were incubated at 27° C.±1° C. at 65 ±5% relative humidity for 10 days.

The wood chips were thawed and sampled to determine the initial moisture level. The chips were then oven dried. A modified chemically defined medium (MCDM) was prepared as described in Leatham, *Mycologia* 75:5, 905-908 (1983). The MCDM medium was then added to 200 grams of oven dried chips in a plastic bag in sufficient quantity to bring the moisture content of the chips up to 60%. The chips were soaked overnight in the added MCDM. The soaked chips were then added to 2800 ml Fernback flasks and the flask covered with aluminium foil. These flasks served as the seed flasks. The seed flasks were autoclaved for 45 minutes. The seed flasks were cooled to room temperature.

The cooled seed flasks were then inoculated with two plugs of one inch square size from a 10-day old fungal culture plate. The inoculated chips were mixed well. Then the seed flasks were incubated for 4 weeks at 27±1° C. at 65±5% moisture content. These incubated seed flasks contained, at the end of their incubation, the seed inoculum for the chips.

The chips for the bulk incubation were thawed, mixed and sampled for moisture content. Sufficient MCDM was added to the chips to bring their moisture content up to 60%. The chips were soaked in the MCDM and then were introduced into the reactor.

Figure 1:
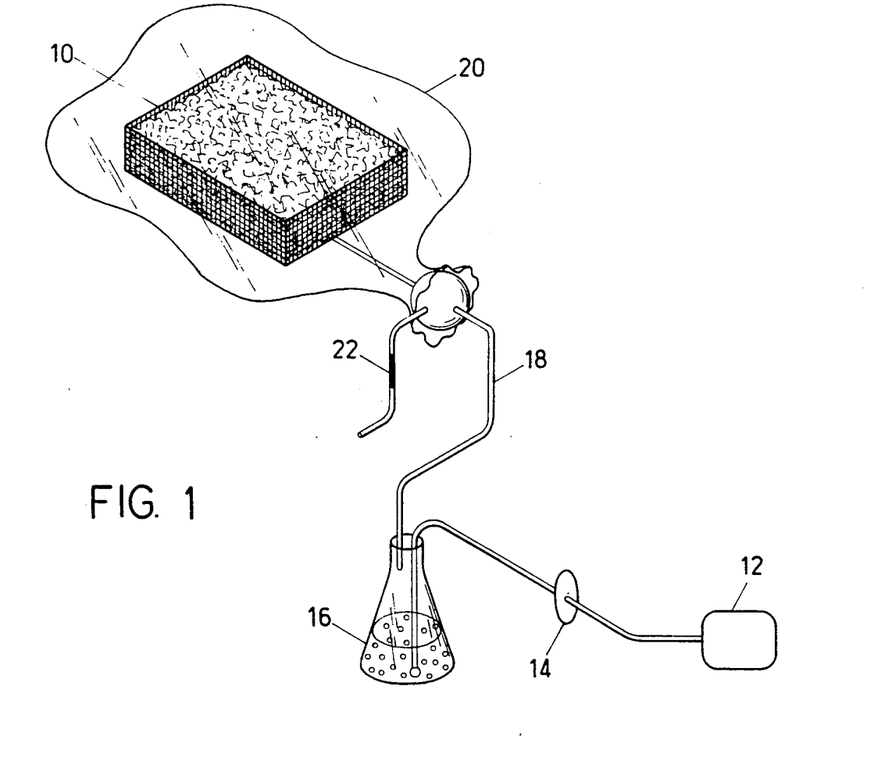
FIG. 1 illustrates the laboratory scale bioreactor used in the illustrative example of the present invention.

The bioreactor used is illustrated in FIG. 1. The receptacle into which the chips were placed was a stainless steel tray 10, constructed of 316 stainless steel in an 8×8 wire mesh and approximately 21×16×3.3 inches in size. An air pump 12 in the form of a Whisper aquarium pump was connected to drive air through a membrane filter 14 of 0.45 pore size and then into a humidification vessel 16. The air inlet into the humidification vessel 16 consisted of a glass tube with a fritted glass gas disperser positioned submerged in water. Humidified air was connected by piping 18 through the inlet to a containment bag 20 which completely surrounded the tray 10. The piping 18 extended down the center of the tray 10 under the chips so that humidified air entered the chip pile. An exit pipe 22 also extended out from the containment bag 20 to allow air to leave. The exit pipe 22 included a tube portion stuffed with glass wool.

The trays 10 were set up in the bags 20 and autoclaved for 30 minutes. The chips and nutrient were then introduced into the bags, 1800 grams for the experimental samples, and 2000 grams for the controls. The soaked chips were then autoclaved for 90 minutes in the bags, and then cooled.

The seed inoculum was then introduced into the bags of the experimental samples, 200 grams of seed inoculum per sample (10% by weight). The inoculum and chips were then mixed and the bioreactors set up as in FIG. 1. The bioreactors were then incubated for 4 weeks at 27±1° C. at 65±5% moisture content with constant aeration with moisture-saturated air.

Mechanical Refining

The control and experimental chips were recovered from the reactors, weighed and sampled for moisture levels. The chips were then hand fed into a 300 mm diameter mechanical single disk refiner with the feed rate adjusted to maintain a constant load on the refiner motor. The feed rate was approximately 574 grams per minute. An integrating watt-hour meter was placed on the refiner to measure total electrical power consumption for each refining batch. The initial refiner plate setting was 18 mills and then clearance was successively reduced to 15, 12, 9, 7, 5, 4.5, 4, 3.5, 3, 2.5, 2 and 1.5 mills in subsequent passes. After each pass, the pulp was collected as it exited the refiner as a hot water pulp slurry. The pulp slurry was dewatered by placement in a porous bag and pressing between passes. Dilution water (80° C.) was added each time as the pulp was fed into the refiner. After the fourth pass and each subsequent pass, the pulp was stored for 30 minutes in the slurry at 2% consistency to remove latency. Samples of the pulp slurry were taken and tested for Canadian Standard Freeness (CSF) at the 7 mil plate setting and smaller, and the sampling continued until the CSF of the pulp dropped below 100 ml.

Figure 2:
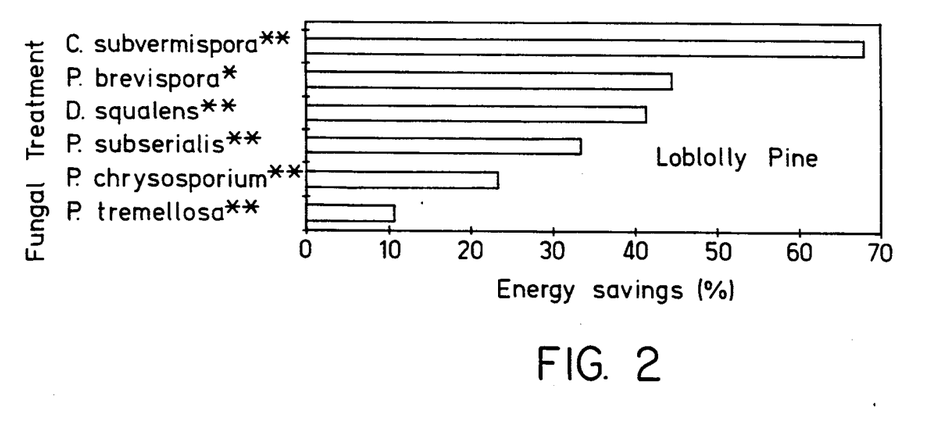
FIG. 2 is a graphical representation of the energy savings achieved in a biopulping process with various fungal species.

The energy consumption required for each experimental sample, and the controls, were compared for constant levels of CSF. These energy saving values were then compared for the various fungi used in the experimental samples, all compared to the common controls. The results are illustrated in the bar graph of FIG. 2. The experimental samples utilizing the *C. subvermispora* were refined into a pulp of a desired level of CSF with 68% less energy than required to refine the control samples. The samples degraded with the other fungi, while better than the control, were less impressive in the amount of energy savings.

Paper Making

To study the paper strength properties of the biomechanical pulps thus created, two samples of 100–200 ml CSF and one sample with a CSF below 100 ml were removed prior to dewatering and used to make paper by hand sheet methods.

The paper hand sheets were made by a standard test technique, TAPPI Standard T205 method. The bursting index of the hand sheets were then measured by the TAPPI Standard T403 method. The internal tearing resistance of the paper was then measured using the TAPPI Standard T414 technique.

For the pulp produced in the stationary bioreactor described below, and degraded with *Ceriporiopsis subvermispora*, the results compared to the control are summarized in the following Table 3. Table 3 also includes the results of a parallel batch of chips degraded by the same fungi in a rotating drum-type bioreactor and refined and made into paper using the same techniques.

TABLE 3

| Sample | Testing of the Paper Made | | |
|---|---|---|---|
| | Energy Used (Whr/kg) | Burst index (kPa-m²/g) | Tear index (mN-m²/g) |
| Control | 2001 | 0.62 | 2.84 |
| C. subvermispora stationary reactor (FIG. 1) | 1167 | 0.82 | 4.75 |
| C. subvermispora rotating reactor | 1353 | 0.80 | 4.85 |

These results demonstrate that regardless of the form of bioreactor, the use of *C. subvermispora* as a pre-treatment to mechanical pulping of pine can achieve not only a dramatic decrease in energy consumption for the pulping, but also an increase in strength of the resulting paper. While other fungal treatments demonstrated some energy savings or some increase in strength of the resulting paper, none exhibited the uniquely advantageous combination of dramatic savings in energy with significantly increased paper strength. These results were achieved with a stationary, and relatively simple and inexpensive, bioreactor design thereby suggesting that a scale-up of this process to commercial scale is feasible.

We claim:

1. A method of making a wood pulp comprising the steps of:
   (a) chipping wood into wood chips;
   (b) introducing the wood chips into a bioreactor;

(c) inoculating the wood chips with an inoculum including a viable culture of the fungus *Ceriporiopsis subvermispora;*

(d) incubating the wood chips under conditions favoring the propagation of the fungus through the wood chips for a sufficient amount of time for the fungus to modify a significant amount of the lignin naturally present in the wood chips; and (e) mechanically pulping the wood chips degraded by the fungus into a paper pulp.

2. A method as claimed in claim 1 wherein the wood chips are of southern yellow pine.

3. A method as claimed in claim 1 wherein the wood chips are of Loblolly pine, *Pinus taeda.*

4. A method as claimed in claim 1 wherein the bioreactor is a stationary location having controllable or defined properties of aeration, humidity and temperature.

5. A method as claimed in claim 1 wherein the bioreactor includes the capability to introduce air into the wood chips therein.

6. A method as claimed in claim 1 wherein the inoculum comprises a quantity of wood chips with the *Ceriporiopsis subvermispora* propagated therein.

7. A method as claimed in claim 1 wherein the *Ceriporiopsis subvermispora* is strain Fp-90031.

8. A method as claimed in claim 1 wherein during the incubating step the conditions include the substantially constant aeration of the wood chips with humidified air.

9. A method of pretreating wood so that the wood may be made into pulp more efficiently comprising the steps of:

(a) chipping the wood into wood chips;

(b) mixing the wood chips with an inoculum which comprises a quantity of wood chips into which has been propagated a viable culture of the fungus *Ceriporiopsis subvermispora;* and (c) incubating the wood chips under conditions favorable to the growth of the fungus in the wood chips for a sufficient period of time for the fungus to modify a portion of the lignin naturally present in the wood chips.

10. A method as claimed in claim 9 wherein the wood chips are of southern yellow pine.

11. A method as claimed in claim 9 wherein the wood chips are of Loblolly pine, *Pinus taeda.*

12. A method as claimed in claim 9 wherein the *Ceriporiopsis subvermispora* is strain Fp-90031.

13. A method as claimed in claim 9 wherein during the incubating step the conditions include the substantially constant aeration of the wood chips with humidified air.

14. A method as claimed in claim 9 wherein the time period of the incubating step is between two to four weeks.

15. A method for producing paper comprising the steps of:

(a) introducing wood chips into a reactor;

(b) inoculating the wood chips in the reactor with a starter inoculum of the fungus *Ceriporiopsis subvermispora;*

(c) incubating the wood chips under conditions favorable to the propagation of the fungus through the wood chips;

(d) mechanically pulping the incubated wood chips to a selected level of freeness of fibers in the pulp; and (e) making paper with the pulp so produced.

16. A method as claimed in claim 15 wherein the wood chips are of southern yellow pine.

17. A method as claimed in claim 15 wherein the wood chips are of Loblolly pine, *Pinus taeda.*

18. A method as claimed in claim 15 wherein the reactor is a stationary location having controllable or defined properties of aeration, humidity and temperature.

19. A method as claimed in claim 15 wherein the bioreactor includes the capability to introduce air into the wood chips therein.

20. A method of claimed in claim 15 wherein the starter inoculum comprises a quantity of wood chips with the *Ceriporiopsis subvermispora* propagated therein.

21. A method as claimed in claim 15 wherein the *Ceriporiopsis subvermispora* is strain Fp-90031.

22. A method as claimed in claim 15 wherein during the incubating step the conditions include the substantially constant aeration of the wood chips with humidified air.

23. A method as claimed in claim 15 wherein the incubating step is performed for between two and four weeks.

24. A method of making paper comprising the steps of:

(a) maintaining in a culture of the fungus *Ceriporiopsis subvermispora;*

(b) making a starter inoculum by (i) inoculating a quantity of starter inoculum wood chips of Loblolly pine with mycelium from the fungal culture; and (ii) incubating the starter inoculum wood chips under conditions of high humidity and generally under conditions favoring and for a time period sufficient for the growth of the fungal culture through the starter inoculum wood chips;

(c) introducing into a stationary bioreactor a quantity of untreated wood chips of Loblolly pine and a quantity of the wood chips from the starter inoculum, the quantity of the starter inoculum wood chips selected so that when added to the quantity of the untreated wood chips, the starter inoculum wood chips are no more than about 10% of the total of the two quantities of wood chips;

(d) incubating the combined quantities of wood chips in the reactor under conditions favorable to the growth of the fungus in the wood chips, such conditions comprising substantially constant aeration with humidified air, and maintenance of at least 60% moisture content in the wood chips, the incubation being maintained until a significant portion of the lignin in the wood chips has been modified;

(e) mechanically pulping the wood chips to a predetermined level of freeness of the fibers in the pulp; and (f) making paper from the pulp so produced.

25. A method as claimed in claim 24 wherein the *Ceriporiopsis subvermispora* used to inoculate the starter inoculum wood chips is maintained on potato dextrose agar slants.

26. A method as claimed in claim 24 wherein the incubating of the starter inoculum wood chips is conducted for a time period of about four weeks.

27. A method as claimed in claim 24 wherein the reactor is a stationary location having controllable or defined properties of aeration, humidity and temperature.

28. A method as claimed in claim 24 wherein the bioreactor includes the capability to introduce air into the wood chips therein.

29. A method as claimed in claim 24 wherein the *Ceriporiopsis subvermispora* is strain Fp-90031.

30. A method as claimed in claim 24 wherein during the incubating step the conditions include the substantially constant aeration of the wood chips with humidified air.

31. A method as claimed in claim 24 wherein the incubating step is performed for between two and four weeks.

* * * * *